(12) United States Patent
Carlson et al.

(10) Patent No.: US 8,181,389 B1
(45) Date of Patent: May 22, 2012

(54) METHOD TO IMPROVE MANUFACTURED SEED GERMINATION BY EXPOSURE TO A CHANGE IN AMBIENT PRESSURE

(75) Inventors: William Carlson, Olympia, WA (US); Craig N. Cootsona, Tacoma, WA (US); Jessie Lynne Wetzbarger, Tacoma, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 158 days.

(21) Appl. No.: 12/727,453

(22) Filed: Mar. 19, 2010

Related U.S. Application Data

(60) Provisional application No. 61/162,892, filed on Mar. 24, 2009.

(51) Int. Cl.
*A01C 1/00* (2006.01)
(52) U.S. Cl. .................................. 47/58.1 SE; 47/57.6
(58) Field of Classification Search ................... 47/57.6, 47/58.1 SE
See application file for complete search history.

(56) References Cited

U.S. PATENT DOCUMENTS

| | | | |
|---|---|---|---|
| 4,957,866 A | 9/1990 | Gupta | |
| 5,034,326 A | 7/1991 | Pullman | |
| 5,036,007 A | 7/1991 | Gupta | |
| 5,041,382 A | 8/1991 | Gupta | |
| 5,236,841 A | 8/1993 | Gupta | |
| 5,294,549 A | 3/1994 | Pullman | |
| 5,427,593 A | 6/1995 | Carlson | |
| 5,482,857 A | 1/1996 | Gupta | |
| 5,563,061 A | 10/1996 | Gupta | |
| 5,564,224 A | 10/1996 | Carlson | |
| 5,687,504 A | 11/1997 | Carlson | |
| 5,701,699 A * | 12/1997 | Carlson et al. | ................. 47/57.6 |
| 5,821,126 A | 10/1998 | Durzan | |
| 6,119,395 A | 9/2000 | Hartle | |
| 6,689,609 B1 | 2/2004 | Fan | |
| 2003/0167684 A1 | 9/2003 | Carlson | |
| 2005/0108936 A1* | 5/2005 | Hartle et al. | ................... 47/57.6 |
| 2006/0032121 A1* | 2/2006 | Hirahara | ........................ 47/57.6 |
| 2007/0016972 A1 | 1/2007 | Rise | |
| 2009/0320360 A1* | 12/2009 | Starr et al. | ..................... 47/57.6 |
| 2010/0154299 A1* | 6/2010 | Kobayashi et al. | ............ 47/57.6 |

OTHER PUBLICATIONS

Davies, High Pressure and Seed Germination, Feb. 1928, American Journal of Botnay, vol. 15, No. 2, pp. 149-156, retrieved from JSTOR: Sep. 30, 2011, http://www.jstor.org/pss/2435659.*
Nakamura et al, Atmospheric Condition Controlling the Seed Germination of an Achlorophyllous Orchid, 1975, Botany Magazine, pp. 103-109.*
Leung, J., and J. Giraudat, "Abscisic Acid Signal Transduction," Annual Review of Plant Physiology and Plant Molecular Biology 49:199-222, Jun. 1998.

* cited by examiner

*Primary Examiner* — Kristen C Hayes
(74) *Attorney, Agent, or Firm* — Weyerhaeuser Law Dept; Rachael Vaughn

(57) ABSTRACT

The invention provides methods for improving the germination of manufactured seeds. The methods comprise the step of subjecting a manufactured seed to at least one change in ambient pressure for a period of time sufficient to generate a conditioned manufactured seed.

20 Claims, 10 Drawing Sheets

METHOD TO IMPROVE MANUFACTURED SEED GERMINATION BY EXPOSURE TO A CHANGE IN AMBIENT PRESSURE

FIELD OF THE INVENTION

The present invention relates to methods for improving the germination of manufactured seeds containing plant embryos.

BACKGROUND

It is often desirable to plant large numbers of genetically identical plants that have been selected to have advantageous properties, but in many cases it is not feasible to produce such plants using standard breeding techniques. In vitro culture of somatic or zygotic plant embryos can be used to produce large numbers of genetically identical embryos that have the capacity to develop into normal plants. However, the resulting embryos lack the protective and nutritive structures found in natural botanic seeds that shelter the plant embryo inside the seed from the harsh soil environment and nurture the embryo during the critical stages of sowing and germination. Attempts have been made to provide such protective and nutritive structures by using manufactured seeds, but so far germination from manufactured seeds is less successful than from natural seeds. Therefore, there is a need for improving rates of conversion for manufactured seeds containing somatic embryos to provide a large number of normal germinants. The present invention addresses this and other needs.

SUMMARY

The present inventors have discovered that subjecting a manufactured seed comprising a plant embryo to at least one change in ambient pressure increases the germination frequency of the manufactured seed. Thus, in one aspect, the present invention provides methods for conditioning a manufactured seed. The methods of this aspect of the invention comprise subjecting a manufactured seed to at least one change in ambient pressure for a period of time sufficient to generate a conditioned manufactured seed, the manufactured seed comprising (a) a plant somatic embryo; (b) a manufactured seed coat enclosing the plant somatic embryo comprising an orifice; and (c) nutritive media in functional contact with the plant somatic embryo, wherein the conditioned manufactured seed has an increased germination frequency in comparison to a manufactured seed that was not subjected to at least one change in ambient pressure. In some embodiments, the manufactured seed further comprises a lid covering the orifice of the seed coat thereby sealing the plant somatic embryo within the manufactured seed.

In another aspect, the present invention provides methods for producing seedlings or full grown plants from plant somatic embryos. The methods of this aspect of the invention comprise (a) inserting a plant somatic embryo into a manufactured seed comprising a manufactured seed coat comprising an orifice and nutritive media, such that the nutritive media is in functional contact with the plant somatic embryo; (b) subjecting the manufactured seed comprising the embryo to at least one change in ambient pressure for a predetermined period of time to generate a conditioned manufactured seed; and (c) planting the conditioned manufactured seed in a growth medium. In some embodiments, the method further comprises sealing the embryo within the manufactured seed prior to step (b).

The methods of the present invention are useful, for example, for conditioning manufactured seeds containing plant somatic embryos, such as conifer somatic embryos (i.e., pine, such as Loblolly pine, fir, or Douglas-fir) to promote physiological maturation of the somatic embryos, and thereby improve the germination rate of the manufactured seeds.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
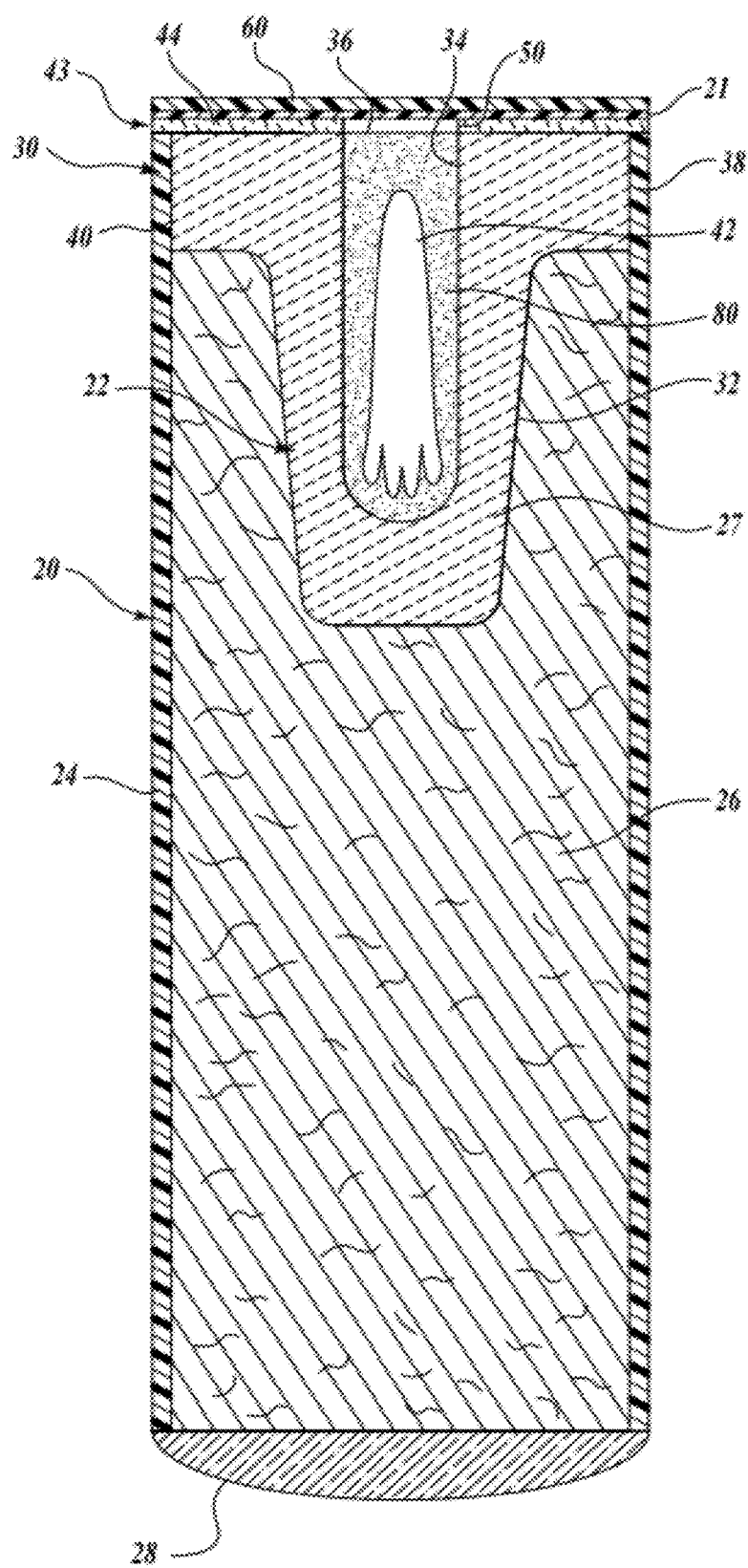
FIG. 1 is a side cross-sectional planar view of an exemplary manufactured seed comprising an embryo for use in the methods of the present invention.

The present disclosure provides methods for conditioning a manufactured seed containing a plant somatic embryo. The methods each include the step of subjecting a manufactured seed comprising a plant somatic embryo to at least one change in ambient pressure for a period of time sufficient to generate a conditioned manufactured seed.

As used herein, "a plant somatic embryo" refers to an embryo produced by culturing totipotent plant cells such as meristematic tissue under laboratory conditions in which the cells comprising the tissue are separated from one another and urged to develop into minute complete embryos. Alternatively, somatic embryos can be produced by inducing "cleavage polyembryogeny" of zygotic embryos. Methods for producing plant somatic embryos suitable for use in the methods of the invention are standard in the art and have been previously described (see, e.g., U.S. Pat. Nos. 4,957,866; 5,034,326; 5,036,007; 5,041,382; 5,236,841; 5,294,549; 5,482,857; 5,563,061; and 5,821,126). For example, plant tissue may be cultured in an initiation medium that includes hormones to initiate the formation of embryogenic cells, such as embryonic suspensor masses that are capable of developing into somatic embryos. The embryogenic cells may then be further cultured in a maintenance medium that promotes establishment and multiplication of the embryogenic cells. Subsequently, the multiplied embryogenic cells may be cultured in a development medium that promotes the development of somatic embryos, which may further be subjected to post-development treatments such as cold-treatments. The somatic embryos used in the methods of the invention have completed the development stage of the somatic embryogenesis process. They may also have been subjected to one or more post-development treatments.

Typically, the plant somatic embryos used in the invention have a shoot end and a root end. In some species of plants, the shoot end includes one or more cotyledons (leaf-like structures) at some stage of development. Plant embryos suitable for use in the methods of the invention may be from any plant species, such as dicotyledonous or monocotyledonous plants or gymnosperms, such as conifer somatic embryos (i.e., pine, such as Loblolly pine, fir, or Douglas-fir).

As used herein, the term "condition" or "conditioning" when used in connection with a plant somatic embryo or a manufactured seed containing a plant somatic embryo means subjecting a plant somatic embryo or a manufactured seed comprising a plant somatic embryo to at least one change in ambient pressure for a period of time sufficient to promote the physiological processes in the somatic embryo which results in germination.

As used herein, the term "germination" refers to a physiological process that results in the elongation of a plant embryo along its axis and is complete when the embryo has elongated to the point of protrusion through the seed coat or manufactured seed lid.

As used herein, the term "complete germination" refers to a manufactured seed having root protrusion through the seed coat or manufactured seed lid.

As used herein, the term "change in pressure" refers to a change in the ambient pressure surrounding a manufactured seed and encompasses a change in positive pressure and/or a change in negative pressure (vacuum). As used herein, the term "positive pressure" refers to a pressure greater than atmospheric pressure. The positive pressure can be measured as pounds per square inch (PSI), which is the amount of force that is exerted on an area of one square inch. Normal atmospheric pressure at sea level is 14.7 PSI. As used herein, the term "negative pressure" refers to a pressure less than atmospheric pressure.

For ease of description, the methods of the present disclosure are described with reference to conditioning a single manufactured seed containing a somatic embryo. It will be understood, however, that typically in the practice of the disclosed methods, numerous manufactured seeds (e.g., tens, hundreds, or thousands) are conditioned together.

In the practice of the present invention, a manufactured seed comprising a plant somatic embryo is subjected to at least one change in ambient pressure for a period of time sufficient to promote the physiological processes in the somatic embryo that result in germination. As demonstrated herein, the present inventors have unexpectedly discovered that subjecting manufactured seeds comprising plant somatic embryos to at least one change in ambient pressure relative to atmospheric pressure for a time period ranging from 1 second up to 96 hours or longer is effective to significantly increase the germination frequency of the manufactured seed, as well as result in an earlier time of germination (root emergence), in comparison to a manufactured seed that was maintained at atmospheric pressure.

A manufactured seed for use in the methods of the invention comprises a plant somatic embryo, a manufactured seed coat, and a nutritive medium. FIG. 1 is a side cross-sectional planar view of an exemplary manufactured seed 20 comprising a plant somatic embryo 42 disposed within for use in the methods of the present invention. As shown in FIG. 1, the embryo 42 is disposed within the cavity 34, is in functional contact with nutritive media 26 and is suitably sealed therein by a live end seal 43. It will be understood that FIG. 1 provides a representative embodiment of a manufactured seed 20 comprising a plant somatic embryo, a manufactured seed coat enclosing the plant somatic embryo comprising an orifice, nutritive media in functional contact with the plant somatic embryo and a lid sealing the plant somatic embryo within the manufactured seed that may be conditioned in accordance with the methods of the invention; however, the method is not limited to the particular embodiment of the manufactured seed shown in FIG. 1.

Figure 2:
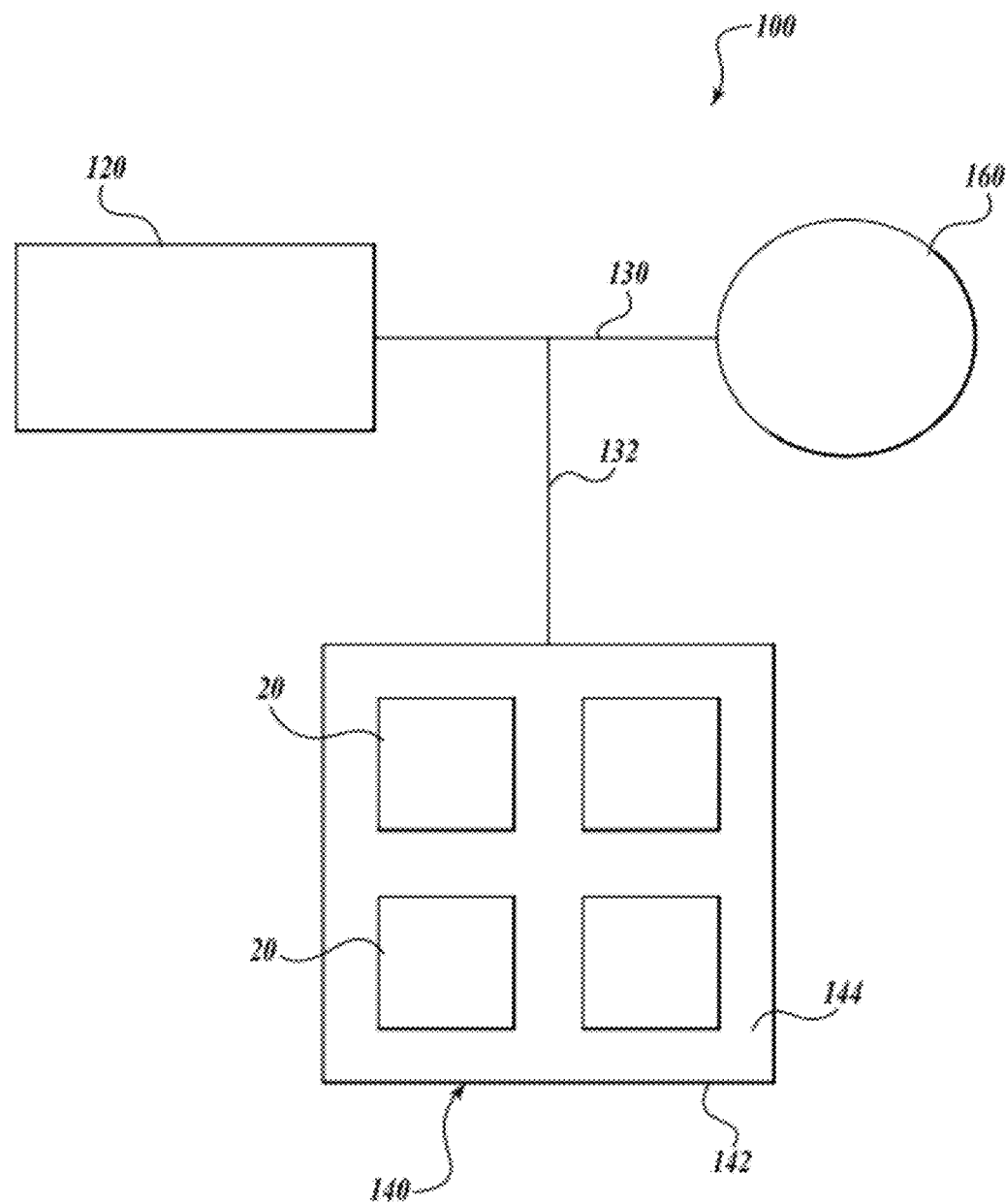
FIG. 2 is a block diagram of an embodiment of a system for conditioning one or more manufactured seed(s) comprising embryos by subjecting the manufactured seeds to at least one change in ambient pressure, in accordance with an embodiment of the present invention.

FIG. 2 shows an example of a system 100 for conditioning a manufactured seed 20 comprising an embryo 42 in order to increase the germination frequency of the manufactured seed 20. As shown in FIG. 2, system 100 includes a pump/vacuum manifold 120 that provides pressure and/or vacuum to the system 100 via a first common tube 130. System 100 also includes one or more pressure/vacuum chambers 140 attached to the first common tube 130 via one or more secondary tube(s) 132. System 100 further optionally includes at least one pressure sensor/recorder 160. As shown in FIG. 2, in one embodiment of the system 100 the at least one pressure sensor/recorder 160 is attached to the first common tube 130. The pressure/vacuum chamber 140 includes a chamber body 142 that defines an interior space 144. As further shown in FIG. 2, one or more manufactured seeds 20, each comprising a somatic embryo 42, are placed inside the interior space 144 of the chamber 140. In some embodiments, the system 100 further comprises one or more of the following: a pressure transducer with output to recording equipment, a thermocoupler, a timer for programmable control, a programmable logic controller, and the like in order to control the rate of change in positive and negative pressure in the system 100.

In operation of the system 100, one or more manufactured seeds 20, each comprising a somatic embryo 42, are placed into the interior space 144 of the chamber body 142 of the pressure/vacuum chamber 140. The system 100 is then pressurized to the desired level (either positive or negative pressure (vacuum) in relation to atmospheric pressure) with the pump/vacuum manifold in order to subject the manufactured seed 20 comprising an embryo 42 to at least one change in ambient pressure for a time period sufficient to condition the manufactured seed(s) to increase germination frequency. It will be understood that FIG. 2 provides a representative embodiment of a system 100 for subjecting a manufactured seed 20 to at least one change in pressure for a period of time sufficient to generate a conditioned manufactured seed in accordance with the methods of the invention; however, the method is not limited to the particular embodiment of the system 100 shown in FIG. 2.

In one embodiment of the method, a vacuum source (i.e., vacuum/pump manifold 120) is activated to apply a negative pressure (vacuum) to the inside of the chamber 140 comprising the manufactured seed(s) 20. When the vacuum source is activated, the pressure inside the chamber 140 is lowered, thereby subjecting the manufactured seed(s) 20 to a decrease in ambient pressure relative to atmospheric pressure. When a desired decrease in pressure is detected by the pressure sensor 160, the vacuum source 120 is either maintained at a desired level or deactivated to allow the pressure level to decay up to atmospheric pressure. The decay of this temporary pressure drop is described as the change in pressure inside the chamber 140 over time. In one embodiment, the method comprises subjecting a manufactured seed to at least one decrease in ambient pressure relative to atmospheric pressure in the range of from about −0.05 PSI to about −4.0 PSI (such as from about −0.5 PSI to about −4.0 PSI, such as from about −2.0 to about −4.0 PSI, such as from about −2.0 PSI to about −3.0 PSI) for a time period sufficient to generate a conditioned manufactured seed. In one embodiment, the method comprises subjecting a manufactured seed to at least one decrease in ambient pressure relative to atmospheric pressure sufficient to increase nutrient flow into the embryo contained in the manufactured seed. In one embodiment, the method comprises subjecting a manufactured seed to at least one decrease in ambient pressure relative to atmospheric pressure sufficient to cause at least one of the lid of the manufactured seed and/or the manufactured seed coat to flex.

In one embodiment of the method, a pressure source (i.e., vacuum/pump manifold 120) is activated to apply a positive pressure to the inside of the chamber 140 comprising the manufactured seed(s) 20. When the pressure source is activated, the pressure inside the chamber 140 is increased, thereby subjecting the manufactured seed(s) 20 to an increase in ambient pressure relative to atmospheric pressure. When a desired increase in pressure is detected by the pressure sensor 160, the pressure source 120 is either maintained at a desired level or deactivated to allow the pressure level to decay back down to atmospheric pressure. The decay of this temporary pressure increase is described as the change in pressure inside the chamber 140 over time. In one embodiment, the method comprises subjecting a manufactured seed to at least one increase in ambient pressure relative to atmospheric pressure in the range of from about +0.05 PSI to about +4.0 PSI (such as from about +0.5 PSI to about +4.0 PSI, such as from about +2.0 to about +4.0 PSI, such as from about +2.0 PSI to about +3.0 PSI) for a time period sufficient to generate a conditioned manufactured seed. In one embodiment, the method comprises subjecting a manufactured seed to at least one increase in ambient pressure relative to atmospheric pressure sufficient to increase nutrient flow into the embryo contained in the manufactured seed. In one embodiment, the method comprises subjecting a manufactured seed to at least one increase in ambient pressure relative to atmospheric pressure sufficient to cause at least one of the lid of the manufactured seed and/or the manufactured seed coat to flex (i.e., move in and/or move out).

In some embodiments, the method comprises subjecting a manufactured seed to at least one pressure/vacuum cycle(s) (such as one cycle, two cycles, three cycles or more), wherein each pressure/vacuum cycle comprises an increase in ambient pressure relative to atmospheric pressure (such as from +0.05 PSI to +4.0 PSI) for a first time period and a decrease in ambient pressure relative to atmospheric pressure (such as from −0.05 PSI to −4.0 PSI) for a second time period.

In accordance with the various embodiments of the method, the manufactured seeds are subjected to a change in ambient pressure for a period of time sufficient to generate a conditioned manufactured seed, such as at least one second up to 96 hours or longer (such as from 5 seconds to 48 hours, or from 10 seconds to 48 hours, or from 30 seconds to 48 hours, 1 minute to 24 hours, from 1 minute to 18 hours, from 30 minutes to 24 hours, or from 1 hour to 48 hours).

A suitable time period sufficient for conditioning a manufactured seed in accordance with the methods of the invention may be determined as described in Example 3 and then applied as the predetermined time period, such as from at least one second up to 96 hours.

In some embodiments, the manufactured seeds are subjected to at least one (such as one, two, three, or more) pressure/vacuum cycle(s) comprising an increase in ambient pressure relative to atmospheric pressure for a first time period ranging from at least one second to 24 hours, followed by a decrease in ambient pressure relative to atmospheric pressure for a second time period ranging from at least one second to 24 hours. In some embodiments, the manufactured seeds are subjected to multiple rapid cycles (such as at least 2, at least 3, or at least 4) of pressure changes, each cycle lasting from about 1 second to 60 seconds each.

In accordance with various embodiments of the methods of the invention, the manufactured seed 20 comprises a plant somatic embryo, a seed coat, nutritive media in functional contact with the plant somatic embryo and optionally, a lid sealing the plant somatic embryo within the manufactured seed. In the exemplary embodiment shown in FIG. 1, the manufactured seed 20 comprises a seed coat 24, nutritive media 26, a dead end seal 28, and an optional cylcap 22 (shoot restraint). The seed coat 24 is suitably formed from a section of tubular material.

In one embodiment the seed coat 24 is made of material that flexes during a change in ambient pressure, such as biodegradable plastic material such as, for example, polylactic acid ("PLA"), or a polycaprolactone ("PCL") mixture, or such as a non-biodegradable plastic material such as a polymer tubing (e.g., polyethylene, neoprene and the like). The seed coat 24 has an opening or orifice that is covered or otherwise occluded by a lid after insertion of the plant embryo. The covered orifice has a lower burst strength than the rest of the seed coat. Thus, a germinating embryo generally emerges from the manufactured seed coat 24 by penetrating through the covered orifice. Typically, the radicle end of the embryo is oriented toward the orifice to facilitate protrusive growth of the primary root of the germinating embryo from the manufactured seed.

The cylcap 22, also known as a restraint, is suitably manufactured from a porous material having a hardness strong enough to resist puncture or fracture by a germinating embryo, such as a ceramic or porcelain material, and includes an end seal portion 30 and a cotyledon restraint portion 32. The cotyledon restraint portion 32 is suitably integrally or unitarily formed with the end seal portion 30. The cylcap 22 also includes a longitudinally extending cavity 34 extending through the end seal portion 30 and partially through one end of cotyledon restraint portion 32. The open end of the cavity 34 is known as a cotyledon restraint opening 36. The cavity 34 is sized to receive a plant embryo 42 therein. As shown in FIG. 1, the cylcap 22 comprises a plurality of pores 27, wherein the pores 27 allow the nutritive media 26 access into the inside of the cavity 34 comprising the embryo 42, and therefore allows the nutritive media 26 to functionally contact the embryo 42 under conditions sufficient to generate a conditioned embryo, as described herein.

The end seal portion 30 is suitably circular when viewed in a top planar view and includes sidewalls 38. The sidewalls 38 may include a tapered portion 40. Although circular is the preferred embodiment of the end seal portion 30, other embodiments and shapes, such as polygonal, square, triangular, oval, and other shapes are also within the scope of the present disclosure.

The live end seal 43 includes a primary end seal 44 and a secondary end seal 21. In some embodiments, the live end seal is made of material that flexes during a change in ambient pressure. The primary end seal 44 is suitably formed from a PCL material described above and includes a centrally located opening 50. The opening 50 is sized to correspond to the diameter of the cavity 34 of the cylcap 22 to permit a germinating embryo 42 to pass therethrough. The primary end seal 44 is suitably attached to the end seal portion 30 by a variety of methods, including glue or heat bonding. The secondary end seal 21 is suitably formed from a well-known sealing material that is capable of flexing during a change in ambient pressure effective to condition a manufactured seed, such a Parafilm®, grafting tape, wax impregnated tissue paper, and the like. The secondary end seal 21 is formed and attached to the primary end seal 44 by a well-known method, such as heat bonding or gluing. In some embodiments, a sealing wax may be used to facilitate bonding between the PCL and the Parafilm. The secondary end seal 21 also includes a predetermined burst strength to permit a germinating embryo 42 to penetrate through the live end seal 44.

As shown in FIG. 1, in some embodiments, the manufactured seed 20 further comprises a tertiary seal 60. In some embodiments, the tertiary end seal 60 is made from a material that is capable of flexing during a change in ambient pressure effective to condition a manufactured seed. The tertiary seal 60 and the live end seal 43 define an outer sealing layer and an inner sealing layer, respectively. The combination of the tertiary seal 60 and the live end seal 43 creates a sealing surface, wherein the sealing layer, defined by the tertiary seal 60, is made from a predetermined material that degrades in structural integrity after a predetermined exposure to environmental conditions. The tertiary seal 60 also serves as an anti-microbial sealant to seal and protect around the embryo as the embryo germinates and emerges from within the seed coat 24 and protects the cotyledon restraint cavity. Suitable materials used to manufacture the tertiary seal 60 include water soluble materials, wax, environmentally degradable materials, and biodegradable materials. In one embodiment, the seed coat 24 and primary end seal 44 are suitably formed from a polyester material, such as biodegradable plastic, such as PCL.

In some embodiments, the method comprises disposing an embryo 42 into the cavity 34 of the cylcap 22, and subjecting the manufactured seed comprising the embryo 42 to at least one change in ambient pressure for a time period sufficient to generate a conditioned manufactured seed prior to sealing the opening 50. In another embodiment, the method comprises disposing an embryo 42 into the cavity 34 of the cylcap 22, sealing the opening 50 and then subjecting the manufactured seed to at least one change in ambient pressure for a time period sufficient to generate a conditioned manufactured seed.

As further shown in FIG. 1, fill material 80 either completely or partially surrounds the embryo 42 and increases the surface area of the embryo 42 in functional contact with the nutritive media 26, thereby providing multiple pathways for the nutrients from the nutritive media 26 to pass to the embryo 42. Although it is preferred that the fill material 80 substantially center the embryo 42 within the cavity 34, the embryo 42 need not be so positioned. The fill material 80 need only position the embryo 42 within the cavity 34 in any manner to place the embryo 42 into functional contact with the nutritive media 26. Further, in some embodiments of the invention, the fill material 80 need only fill, either completely or partially, one or two sides of the space between the embryo 42 and the walls of the cavity 34.

Preferably, the fill material 80 is an absorbent, such as activated charcoal, Dowex resins, zeolites, alumina, clay, diatomaceous earth, silica gel, and Kieselguhr. During assembly of the manufactured seed 20, the fill material 80 is deposited into the cavity 34 of the cylcap 22 in any manner known in the art, including manually. The fill material 80 is preferably, but not necessarily, deposited within the cavity 34 such that it substantially centers the embryo 42 within the cavity 34. Centering the embryo 42 within the cavity 34 increases the surface area of the embryo 42 in functional contact with the nutritive media 26. As used herein, the term "functional contact" is intended to mean in a position where the embryo 42 uptakes nutrients from the nutritive media 26. An exemplary method for preparing fill material 80 for insertion into the cavity 34 is provided in Example 1.

In accordance with the methods of the invention, nutritive media 26 is in functional contact with the plant somatic embryo disposed within the manufactured seed 20. As used herein, a "nutritive medium" refers to a source of nutrients, such as vitamins, minerals, carbon, and energy sources, and other beneficial compounds used by the embryo during germination. Thus, the nutritive medium is analogous to the gametophyte of a natural seed. A nutritive medium according to the invention may include a substance that causes the medium to be a semisolid or have a congealed consistency under normal environmental condition.

The nutritive medium typically comprises one or more carbon sources, vitamins, and minerals. Suitable carbon sources include, but are not limited to, monosaccharides, disaccharides, and/or starches. The nutritive medium may also comprise amino acids, an adsorbent composition, and a smoke suspension. Suitable amino acids may include amino acids commonly found incorporated into proteins as well as amino acids not commonly found incorporated into proteins, such as argininosuccinate, citrulline, canavanine, ornithine, and D-steroisomers. Suitable adsorbent compositions include, but are not limited to, charcoal, polyvinyl polypyrolidone, and silica gels. A suitable smoke suspension contains one or more compounds generated through the process of burning organic matter, such as wood or other cellulosic material. Solutions containing these by-products of burning organic matter may be generated by burning organic matter, washing the charred material with water, and collecting the water. Solutions may also be obtained by heating the organic matter and condensing and diluting volatile substances released from such heating. Certain types of smoke suspensions may be purchased from commercial suppliers, for example, Wright's Concentrated Hickory Seasoning Liquid Smoke (B&G Foods, Inc., Roseland, N.J. 07068). Smoke suspension may be incorporated into the nutritive medium in any of various forms. For instance, smoke suspension may be incorporated as an aerosol, a powder, or as activated clay. An exemplary concentration of Wright's Concentrated Hickory Seasoning Liquid Smoke liquid smoke suspension, if present, is between 0.0001 ml and 1 ml of smoke suspension per liter of medium. The nutritive medium may also include one or more compounds involved in nitrogen metabolism, such as urea or polyamines.

The nutritive medium may include oxygen-carrying substances to enhance both the absorption of oxygen and the retention of oxygen by the nutritive medium, thereby allowing the medium to maintain a concentration of oxygen that is higher than would otherwise be present in the medium solely from the absorption of oxygen from the atmosphere. Exemplary oxygen-carrying substances are described in U.S. Pat. No. 5,564,224, herein incorporated by reference.

The nutritive medium may also contain hormones. Suitable hormones include, but are not limited to, abscisic acid, cytokinins, auxins, and gibberellins. Abscisic acid is a sesquiterpenoid plant hormone that is implicated in a variety of plant physiological processes (see, e.g., Milborrow, *J. Exp. Botany* 52:1145-1164, 2000; Leung & Giraudat, *Ann. Rev. Plant Physiol. Plant Mol. Biol.* 49:199-123, 1998). Auxins are plant growth hormones that promote cell division and growth. Exemplary auxins for use in the germination medium include, but are not limited to, 2,4-dichlorophenoxyacetic acid, indole-3-acetic acid, indole-3-butyric acid, naphthalene acetic acid, and chlorogenic acid. Cytokinins are plant growth hormones that affect the organization of dividing cells. Exemplary cytokinins for use in the germination medium include, but are not limited to, e.g., 6-benzylaminopurine, 6-furfurylaminopurine, dihydrozeatin, zeatin, kinetin, and zeatin riboside. Gibberellins are a class of diterpenoid plant hormones (see, e.g., Krishnamoorthy, Gibberellins and Plant Growth, John Wiley & Sons, 1975). Representative examples of gibberellins useful in the practice of the present invention include gibberellic acid, gibberellin 3, gibberellin 4 and gibberellin 7. An example of a useful mixture of gibberellins is a mixture of gibberellin 4 and gibberellin 7 (referred to as gibberellin 4/7), such as the gibberellin 4/7 sold by Abbott Laboratories, Chicago, Ill.

When abscisic acid is present in the nutritive medium, it is typically used at a concentration in the range of from about 1 mg/L to about 200 mg/L. When present in the nutritive medium, the concentration of gibberellin(s) is typically between about 0.1 mg/L and about 500 mg/L. Auxins may be used, for example, at a concentration of from 0.1 mg/L to 200 mg/L. Cytokinins may be used, for example, at a concentration of from 0.1 mg/L to 100 mg/L.

Typically, the nutritive medium is in the form of a hydrated gel. A "gel" is a substance that is prepared as a colloidal solution and that will, or can be caused to, form a semisolid material. Such conversion of a liquid gel solution into a semisolid material is termed herein "curing" or "setting" of the gel. A "hydrated gel" refers to a water-containing gel. Such gels are prepared by first dissolving in water (where water serves as the solvent, or "continuous phase") a hydrophilic polymeric substance (serving as the solute, or "disperse phase") that, upon curing, combines with the continuous phase to form the semisolid material. Thus, the water becomes homogeneously associated with the solute molecules without experiencing any substantial separation of the continuous phase from the disperse phase. However, water molecules can be freely withdrawn from a cured hydrated gel, such as by evaporation or imbibition by a germinating embryo. When cured, these gels have the characteristic of compliant solids, like a mass of gelatin, where the compliance becomes progressively less and the gel becomes more "solid" to the touch as the relative amount of water in the gel is decreased.

Exemplary nutritive media are described in U.S. Pat. No. 5,687,504 and in U.S. patent application Ser. No. 10/371,612, herein incorporated by reference. A representative nutritive medium is KE64, the composition of which is set forth in Table 1 below.

The methods of this aspect of the invention produced conditioned manufactured seeds comprising somatic plant embryos having an increased germination frequency in comparison to manufactured seeds that are not exposed to at least one change in ambient pressure for a time period sufficient to generate a conditioned embryo, as further described and demonstrated in Examples 1-4 herein.

In another aspect, the present invention provides methods for producing seedlings or full grown plants from plant somatic embryos. The methods according to this aspect of the invention comprise (a) inserting a plant somatic embryo into a manufactured seed comprising a manufactured seed coat comprising an orifice and nutritive media, such that the nutritive media is in functional contact with the plant somatic embryo; (b) subjecting the manufactured seed comprising the embryo to at least one change in ambient pressure for a predetermined period of time to generate a conditioned manufactured seed; and (c) planting the conditioned manufactured seed in a growth medium. In some embodiments, the method further comprises sealing the embryo within the manufactured seed prior to step (b). A manufactured seed comprising a somatic plant embryo may be produced using the methods described herein. The manufactured seeds may be subjected to a change in ambient pressure, such as from −4.0 PSI to +4.0 PSI using any suitable method, such as with the system 100 described herein. A suitable time period sufficient for conditioning a manufactured seed in accordance with the methods of the invention may be determined as described in Example 3 and then applied as the predetermined time period, such as from at least one second up to 96 hours. After exposure to the at least one change in ambient pressure, the conditioned manufactured seeds can be germinated, for example, on a solid germination medium such as a basal medium lacking growth hormones, for sufficient time under environmental conditions of 23° C. to 25° C., until the resulting plantlets have a well-developed radicle and hypocotyls and green cotyledonary structure and epicotyl. The germinated plants can be transferred to a growth medium, such as a tissue culture growth medium or soil, such as potting soil, for further growth. For example, the germinated plants can be planted in soil in a greenhouse and allowed to grow before being transplanted to an outdoor site. In another embodiment, after exposure to the at least one change in ambient pressure, the conditioned manufactured seeds can be planted into a growth medium where they germinate and grow into plants (e.g., sown outdoors in bareroot nurseries). In some embodiments of this aspect of the invention, a plant somatic embryo is sealed within the manufactured seed and stored for a period of time, such as from at least one hour, at least one day up to at least one week, from one month to 12 months, up to a year or longer, until just prior to planting, at which time the stored manufactured seed is conditioned by subjecting the manufactured seed to at least one change in ambient pressure to generate a conditioned embryo.

The following examples merely illustrate the best mode now contemplated for practicing the invention, but should not be construed to limit the invention.

EXAMPLE 1

This Example demonstrates that exposing a manufactured seed comprising a somatic embryo to a cycle of positive and negative pressure improves germination frequency.

Methods:

Somatic embryos: Somatic embryos of Loblolly pine genotype A were grown in liquid culture then plated on a development medium and incubated for a period of 12 weeks, followed by incubation for 4 weeks on a stratification medium at 4° C. At the end of this sequence, embryos were loaded into a manufactured seed as described below.

Manufactured Seed:

Representative methods used for making manufactured seeds are described in U.S. Pat. Nos. 6,119,395; 5,701,699; and 5,427,593, incorporated herein by reference.

Manufactured seeds were prepared with KE 64 agar nutritive medium, as shown below in Table 1, with sucrose (50 g/L) of sucrose, agar (18 g/L to 26 g/L), nutrient-loaded charcoal (60 g/L) and Pluronic F68 (10 g/L).

The manufactured seeds used in this Example included a seed coat 24, nutritive medium and a plant embryo 42. Nutritive medium is analogous to the gametophyte of a natural seed. A manufactured seed that does not include the plant embryo is known in the art as a "seed blank." The seed blank typically is a cylindrical capsule having a closed end and an open end. The synthetic gametophyte is placed within the seed coat to substantially fill the interior of the seed coat. A longitudinally extending hard porous insert, known as a cotyledon restraint 22, was centrally located within one end of the seed coat, surrounded by the synthetic gametophyte, and included a centrally located cavity extending partially through the length of the cotyledon restraint.

The cavity 34 was sized to receive the plant embryo 42 therein. The well-known plant embryo includes a radicle end and a cotyledon end. The plant embryo was deposited within the cavity of the cotyledon restraint 22, cotyledon end first. The plant embryo was then sealed within the seed blank by an end seal 43. There was a weakened spot in the end seal 43 to allow the radicle end of the plant embryo to penetrate the end seal.

The end seal 43 (lid) was attached to the manufactured seed by stretching a wax base film, such as Parafilm™ (Pechiney Plastic Packaging, Chicago, Ill. 60631). Alternatively, the end seal may be attached to the manufactured seed by forming a wax seal to enclose the embryo within the manufactured seed. Additionally, to protect against microbial invasion, the end seals were treated with a tribiotic ointment.

The nutritive medium KE 64 (see Table 1) was prepared from pre-made stocks. The required amount of each stock solution (that is not heat-labile) was added to water. Nonstock chemicals (such as charcoal, and agar) were weighed out and added directly to the solution. After all the nonheat-labile chemicals and compounds were added, the medium was brought up to an appropriate volume and the pH was adjusted. The medium was then sterilized by autoclaving. Filter-sterilized heat-labile components (such as sucrose, amino acids, and vitamins) were added after the medium had cooled.

With reference to FIG. 1, fill material 80 for insertion into the cavity 34 of the manufactured seed was prepared by combining approximately 7.0 g of activated charcoal with 246 ml of nutritive media (KE64) to create a mixture. The formulation of KE64 nutritive media is provided below in TABLE 1.

TABLE 1

Formulation of KE64 Nutritive Media

| Medium Component | Final Concentration (mg/l) | Amount to add for 300 ml |
|---|---|---|
| $NH_4NO_3$ | 301.1 | 2.2 ml |
| $H_3BO_3$ | 10.0 | 0.75 ml |
| $(NH_4)_2MoO_4$ | 0.06 | |
| $CaCl_2—2H_2O$ | 299.2 | 1.00 ml |
| $KH_2PO_4$ | 1800.0 | 7.5 ml |
| $MgSO_4—7H_2O$ | 1000.0 | |
| $MnCl_2·4H_2O$ | 6.0 | 0.75 ml |
| $ZnSO_4—7H_2O$ | 0.8 | |
| $CuCl_2—2H_2O$ | 0.5 | |
| Ferric Citrate | 60 mg/l | 0.75 ml |

The mineral stocks were added to the KE64 media, the mixture was autoclaved for about 25 minutes, then the sucrose solution (30 ml of a 50% stock solution) and organic stocks were added to the mixture. One such organic stock formulation is provided below in TABLE 2.

TABLE 2

| Medium Component | Final Concentration mM | Final Concentration (mg/l) | Amount to add for 300 ml complete media |
|---|---|---|---|
| Myo-inositol | 0.5549 | 100.0 | 3.0 ml |
| Thiamine-HCl | 0.0030 | 1.0 | |
| Pyridoxine-HCl | 0.0012 | 0.25 | |
| Nicotinic acid | 0.0081 | 1.0 | |
| Riboflavin | 0.0021 | 0.125 | |
| Ca-pantothenate | | 0.50 | |
| Biotin | 0.0003 | 0.0010 | |
| Folic acid | 0.8077 | 0.1250 | |

TABLE 2-continued

| Medium Component | Final Concentration mM | Final Concentration (mg/l) | Amount to add for 300 ml complete media |
|---|---|---|---|
| L-asparagine | 1.8255 | 106.7 | 3.0 ml |
| L-glutamine | 0.3646 | 266.7 | |
| L-lysine-2HCl | 0.7612 | 53.3 | |
| DL-serine | 0.4631 | 80 | |
| L-proline | 1.5310 | 53.3 | |
| L-arginine-HCl | 0.4552 | 266.7 | |
| Urea | 13.3200 | 800 | |
| L-valine | 0.5983 | 53.3 | 3.0 ml |
| L-alanine | 0.2203 | 53.3 | |
| L-leucine | 0.2448 | 80 | |
| L-threonine | 0.3226 | 26.7 | |
| L-phenylalanine | 0.1720 | 53.3 | |
| L-histidine | 0.1308 | 26.7 | |
| L-tryptophan | 0.2035 | 26.7 | |
| L-isoleucine | 1.2930 | 26.7 | |
| L-methionine | 0.7100 | 26.7 | |
| L-glycine | 0.0003 | 53.3 | |
| L-tyrosine | 0.2242 | 53.3 | 0.75 ml |
| L-cysteine | 0.6098 | 26.7 | 0.75 ml |

The mixture was filtered through well-known filter paper and the fill material 80 (e.g., charcoal) was harvested from the filter paper. The harvested fill material 80 was then dried until it became flowable matter. The dry, nutrient loaded charcoal fill material was loaded into the restraint and the embryo was inserted into the charcoal filled area.

All seeds were lidded the morning following insertion/charcoaling. Live ends were dipped in blue wax mixture. Wax was used as a light coating between the primary and secondary end seals to promote good bonding.

Vacuum/Pressure Conditioning System

The following system was used in this and subsequent Examples, unless stated otherwise. With reference to FIG. 2, in the system 100, multiple pressure/vacuum chambers 140 (i.e., 60 cc syringes) were connected via a common tube 130 to a pump/vacuum manifold 120 (i.e., one common feed syringe on a syringe pump). Twelve manufactured seeds 20 were placed into the interior space 144 of the chamber 140 (i.e., into the barrel of each 60 cc syringe). Syringes were then pressurized at a rate of 0.5 ml/hr each and held overnight. In this experiment, since one common feed syringe was connected to the pump/vacuum manifold 140, the common syringe was pressurized at a rate of 3.0 ml/hr (6 syringes×0.5) to account for the manifold setup. The change in ambient pressure was measured via a pressure sensor 160 attached to the system 100.

Experimental Conditions Tested

In this example, the following conditions were tested, with 12 manufactured seeds tested per condition.

1. Manufactured seed with nutritive media and charcoal in cavity, placed in the syringe environment within the vacuum/pressure conditioning system.

2. Manufactured seed with nutritive media, no charcoal in cavity, placed in a syringe environment within the vacuum/pressure conditioning system.

3. Manufactured seed with nutritive media and charcoal in cavity, placed in a dessicator sealed from any pressure change (on a lab bench).

4. Manufactured seed with nutritive media, no charcoal in cavity, placed in a dessicator sealed from any pressure change (on a lab bench).

For the Syringe environment, a 60 cc syringe with 12 seeds in each was connected to a syringe pump manifold. One pressure change occurred per day at a rate of 0.5 ml/hr overnight. For the control environment, manufactured seeds were placed in a dessicator (but with no vacuum applied) and left sitting on a lab bench overnight, sealed from any pressure change to maintain constant air pressure.

In this experiment, after treatment the manufactured seeds were left in the syringe environment to germinate. Manufactured seeds were examined at seven days post treatment for signs of germination.

Results:

It was unexpectedly observed that by day six after the vacuum/pressure treatment that 100% of the manufactured seeds containing genotype A embryos (12/12) placed in the syringe environment within the vacuum/pressure conditioning system had completely germinated, as measured by radicle emergence, and had exited the lid. In contrast, none (0%) of the 12 control genotype A manufactured seeds that were maintained at constant pressure had germinated by day six. By day eight, only 18% of the control genotype A manufactured seeds had germinated. This rapid and high frequency germination after exposure to a change in ambient pressure was particularly surprising because this experiment was carried out with genotype A of Loblolly pine, which was known to typically have a very low germination frequency under standard conditions (i.e., not exposed to a pressure change). It was also observed that the lids on the manufactured seeds that were subjected to the pressure change were in either inverted or protruding positions, which suggests that the seed construct (e.g. the lid and/or the seed coat) moved to compensate for the change in pressure. While not wishing to be bound by any particular theory, it is hypothesized that the change in ambient pressure drives the nutritive media present in the manufactured seed into the cotyledons and improves vigor enough to allow embryos to germinate at a higher frequency than embryos that are not exposed to a change in ambient pressure.

EXAMPLE 2

This Example shows a representative method of the invention for conditioning (i.e., improving the germination by exposure to a change in ambient pressure) of manufactured seeds containing Loblolly pine somatic embryos.

Methods:

The vacuum/pressure conditioning system was set up as described in Example 1, with a pressure transducer and voltmeter attached to the system with output to a digital voltmeter recorder to produce data on the pressure inside the system. The common feed syringe was set such that the plunger was half way down the syringe barrel, so that it would be pushed and pulled by the pump/vacuum manifold 140.

Fourteen manufactured seeds from Genotype B of Loblolly pine were treated per condition listed below. The manufactured seeds and embryos were prepared as described in Example 1. In this experiment, about ⅓ of the cavity 34 was filled with fill material 80 after insertion.

Treatment Conditions for Manufactured Seeds:

1. Pressure/Vacuum Cycling (in a Syringe Environment)

Figure 3:
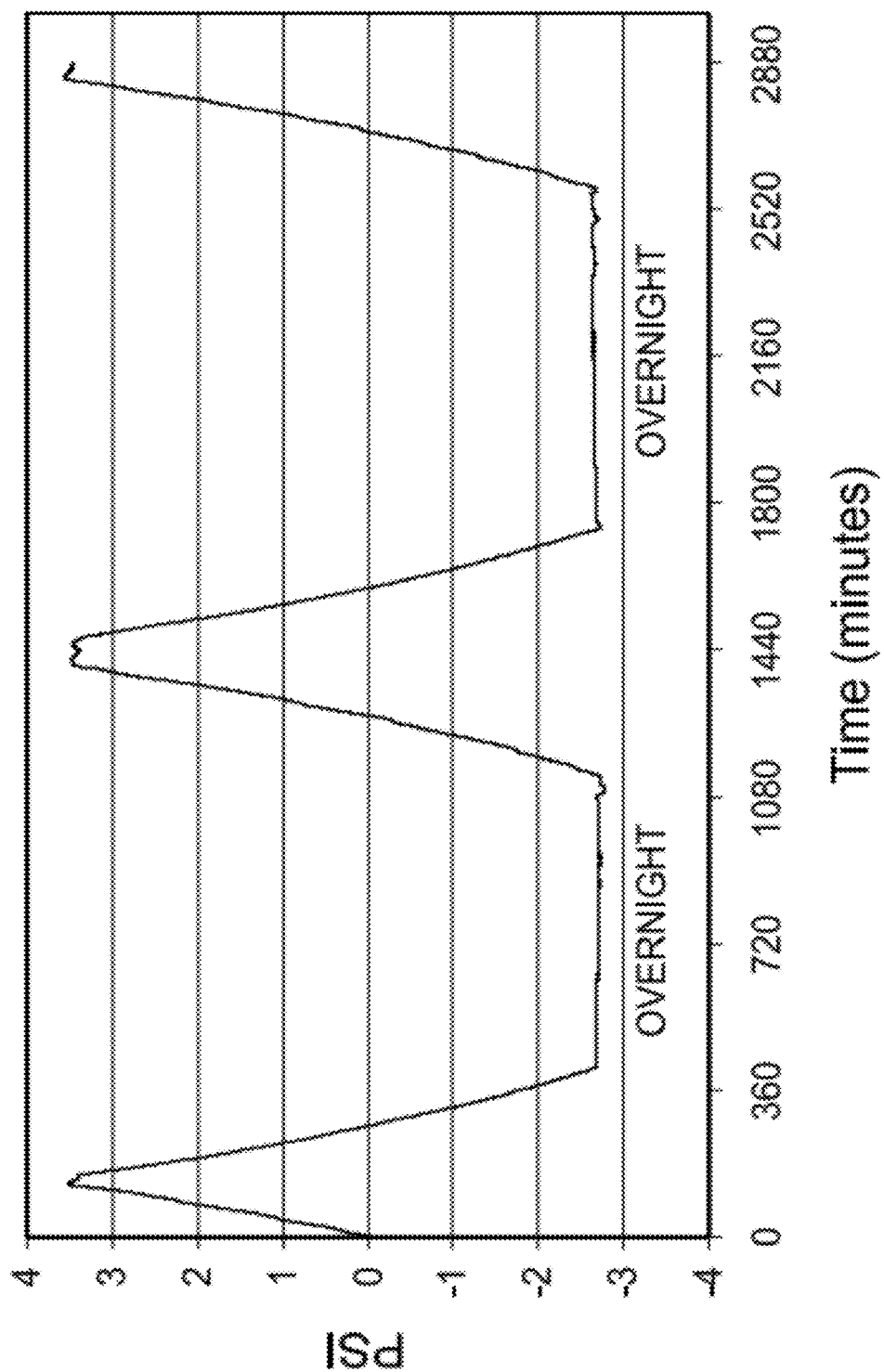
FIG. 3 graphically illustrates the positive and negative changes in ambient pressure (PSI) relative to atmospheric pressure that the manufactured seeds were subjected to, as measured in one minute intervals over a 48-hour treatment period, as described in Example 2.

A total of 14 manufactured seeds were placed into a syringe environment within the vacuum/pressure conditioning system. The plunger of the common feed syringe was set to move at a rate of 2 mL/hour, which correlated to a maximum pressure change of from −3.0 PSI to +3.5 PSI over the course of the 48-hour treatment (in the context of the system containing two 60 cc syringes and a transducer). The pressure/vacuum measurements taken at one-minute intervals recorded over the 48-hour time period of the experiment are shown in FIG. 3. When starting at the mid point, the plunger of the common feed syringe was set to move at a rate of 2 mL/hour, which correlates to a maximum pressure change of from −3 PSI to +3.5 PSI over the course of the experiment, in the context of the system containing two 60 cc syringes and a transducer. As shown in FIG. 3, over the course of the 48-hour treatment, the manufactured seeds were exposed to the +3.0 PSI to +3.5 PSI peak level three times, each separated by exposure to the −2.5 PSI to −3.0 PSI vacuum levels, resulting in a sequence of exposure to a positive pressure ranging from +0.05 PSI to +3.5 PSI for a first time period of about six hours, exposure to a negative pressure (i.e., vacuum) ranging from −0.05 PSI to −3.0 PSI for a second time period of about 18 hours, exposure to a positive pressure ranging from 0.05 PSI to +3.5 PSI for a third time period of about six hours, and exposure to a negative pressure ranging from −0.05 PSI to −3.0 PSI for a fourth time period of about 18 hours, and exposure to a positive pressure ranging from +0.05 PSI to +3.5 PSI for a fifth time period of about three hours.

2. No Pressure Change (in a Syringe Environment)

A total of 14 manufactured seeds were placed inside a syringe that was held at atmospheric pressure (0 PSI).

3. Pressure Cycle Only (in a Syringe Environment)

A total of 14 manufactured seeds were placed into a syringe environment within the vacuum/pressure conditioning system, and the pump was set to only provide a positive change in pressure from a range of 0.0 PSI up to a maximum of +3.5 PSI over a 48-hour time period.

4. Vacuum Cycle Only (in a Syringe Environment)

A total of 14 manufactured seeds were placed into a syringe environment within the vacuum/pressure conditioning system, and the pump was set to only provide a negative change in pressure (i.e., a vacuum) from a range of 0.00 PSI to a minimum pressure of −3.0 PSI over a 48-hour time period.

5. No Pressure Change (in Petri Dish on Lab Bench)

A total of 14 manufactured seeds were placed into a petri dish without media in the plate, which was sealed with one wrap of Parafilm™ and left on a laboratory bench, thereby exposed to atmospheric pressure, with no induced pressure change, over a 48-hour time period.

Germination

After the 48-hour treatments shown above, the manufactured seeds were left inside the treatment environments and the percent germination, as measured by the presence of root emergence from the lid, was determined at days 13 and 21.

Figure 4A:
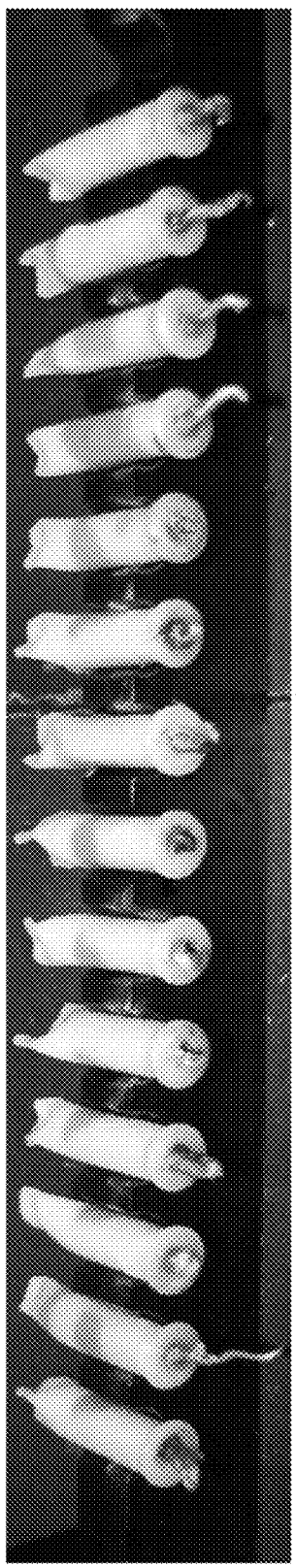
FIG. 4A is a photograph showing germination of 14/14 (100%) of the conditioned manufactured seeds measured 19 days after they were subjected to a cycle of positive and negative change in ambient pressure over a 48-hour time period, as described in Example 2.

Results:

FIG. 4A is a photograph of the manufactured seeds from treatment #1 taken 19 days after treatment. As shown in FIG. 4A, 14/14 (100%) of the manufactured seeds from treatment #1 (pressure/vacuum cycle) germinated by day 19, as measured by radicle emergence from the lid.

Figure 4B:
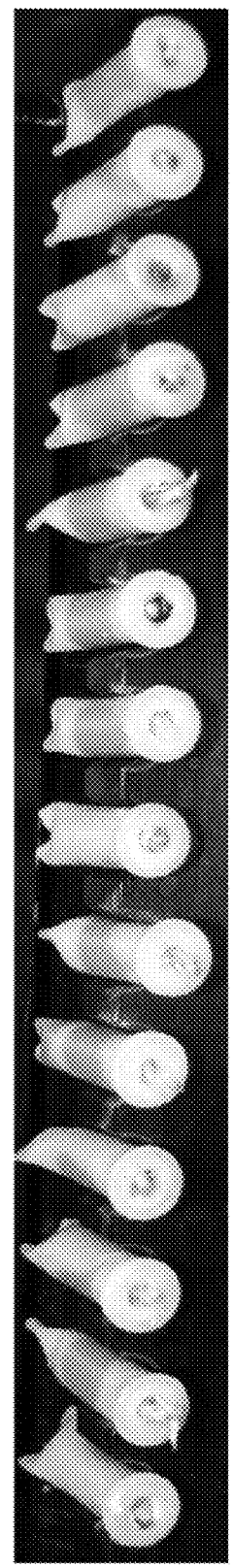
FIG. 4B is a photograph showing germination of 4/14 (28.5%) of the control, non-conditioned, manufactured seeds measured 19 days after they were maintained at atmospheric pressure over a 48-hour time period, as described in Example 2.

FIG. 4B is a photograph of the manufactured seeds from treatment #2 taken 19 days after treatment. As shown in FIG. 4B, 4/14 (28.5%) of the manufactured seeds from treatment #2 (control, no pressure change) germinated by day 19, as measured by radicle emergence from the lid.

TABLE 3 below provides the percent germination at day 13 and day 21 after treatment for treatment conditions #1 to #5.

TABLE 3

Effect of Treatments 1-5 on the Germination Frequency of Manufactured Seeds containing Loblolly Genotype A embryos

| Treatment | Day 13: % Germination (Root Emergence from lids) | Day 21: % Germination (Root emergence from lids) |
|---|---|---|
| 1: alternating pressure and vacuum | 52% | 70% |
| 2: neither pressure nor vacuum (atmospheric pressure maintained in syringe) | 12% | 35% |
| 3: pressure only in syringe environment | 21% | 42% |
| 4: vacuum only in syringe environment | 8% | 35% |
| 5: lidded non-humidified petri plate on bench (atmospheric pressure maintained) | 0% | 21% |

As demonstrated by the results shown in FIGS. 4A, 4B and TABLE 3, the manufactured seeds from treatment #1, which were conditioned by exposure to an alternating cycle of increased pressure and decreased pressure (vacuum), had the highest frequency of germination (100% germination at day 19) and also the most rapid onset of germination in comparison to the manufactured seeds from control treatment #2, which were not exposed to a change in pressure (28.5% germination at day 19). Pressure only (treatment #3) or vacuum only (treatment #4) appeared to produce a modest improvement over the negative control, but root emergence and embryo performance in this experiment were not different enough to provide statistically significant evidence to support this hypothesis. Therefore, the overall conclusion from this experiment is that exposing manufactured seeds to alternating pressure and vacuum provides a synergistic effect on the percentage of root penetration.

It is interesting to note that the manufactured seeds that were incubated in a non-humidified petri plate sitting on the bench at atmospheric pressure (control treatment #5) had no root emergence at all by day 13 (0% germination), in contrast to the manufactured seeds that were incubated in a capped syringe environment (treatment #2), which had a germination frequency of 12% by day 13, as shown in TABLE 3. Therefore, it appears that a 48-hour incubation of manufactured seeds in a syringe environment yields manufactured seeds with higher germination frequencies than a 48-hour incubation in a lidded, nonhumidified petri plate. Further in this regard, it is noted that the relative humidity of the capped syringe and the petri plate were monitored over the course of this experiment. As expected, it was determined that the relative humidity in the closed syringe environment was much greater (about 90%) than the petri plates on the lab bench (below 60%) (data not shown). Therefore, it is likely that the lower frequency of germination (i.e., root emergence) in the manufactured seeds after incubation in the petri plates can be attributed to the lower relative humidity, causing the embryos to become too dry and thereby reducing menisci sizes and nutrient transfer between embryo and seed restraint.

Additional treatment conditions were run in parallel to treatments #1 to #5 in order to determine whether pressure and vacuum would have an effect on the germination of bare embryos (not loaded into in a manufactured seed) that were stored on solid nutritive media, either with all the cotyledons in contact with the media, or with bare embryos laid on their sides on the media in small vials, covering the vials with a single piece of Parafilm™ (to replicate the flexibility of the Parafilm™ lid on the manufactured seeds, then putting the vials inside a syringe environment.

It was determined that there was no significant difference in germination (i.e., root emergence) and embryo performance for bare embryos exposed to pressure and vacuum as compared to those that were maintained at atmospheric pressure (data not shown). Therefore, based on these results it appears that the manufactured seed construct surrounding the embryo plays a role in translating an increase and decrease in ambient pressure on the manufactured seed into improved performance of the embryo contained inside the manufactured seed, likely via movement of the flexible lid, and/or the somewhat flexible seed coat, to create an effect (i.e., an improvement in germination frequency) not seen on bare embryo exposed to the same pressure treatments.

In summary, germination, as measured by root emergence from manufactured seed, was observed to occur at a much higher frequency after exposure of the manufactured seeds to alternating pressure and vacuum. The alternating pressure and vacuum provided a synergistic effect that increased the percent root emergence more than the sum of treatment with vacuum alone and the treatment with pressure alone. The data from this experiment further demonstrates that manufactured seeds exposed to positive pressure only, or to vacuum only, tended to have a higher frequency of root emergence than manufactured seeds maintained at atmospheric pressure.

While not wishing to be bound by any particular theory, it is believed that the pressure change increased nutrient perfusion into the embryo from the manufactured seed and increased movement from the gametophyte medium, thereby increasing the frequency of germination in comparison to manufactured seeds that were maintained at atmospheric pressure. Therefore, prior to sowing, manufactured seeds comprising embryos that are exposed to a pressure change in the form of positive pressure, negative pressure, or a cycling between positive and negative pressure would be expected to have a higher frequency and speed of germination in comparison to manufactured seeds that were maintained at constant pressure.

EXAMPLE 3

This example describes the results of electron probe microanalysis that was performed on manufactured seeds exposed to the various treatment conditions described in Example 2, which confirm that pressure and vacuum treatment of manufactured seeds resulted in an increased tissue concentration of nutrients.

Methods:

Manufactured seeds containing embryos of Loblolly Pine, Genotype C, were prepared as described in Example 1, and were subjected to pressure/vacuum cycling treatment #1 or control treatment #2, as described in Example 2.

After treatment, the embryos were excised from the manufactured seeds, cross-sectioned, and analyzed by scanning electron microscopy via electron probe microanalysis at the level of 300 μm and 100 μm resolution.

Figure 5A:
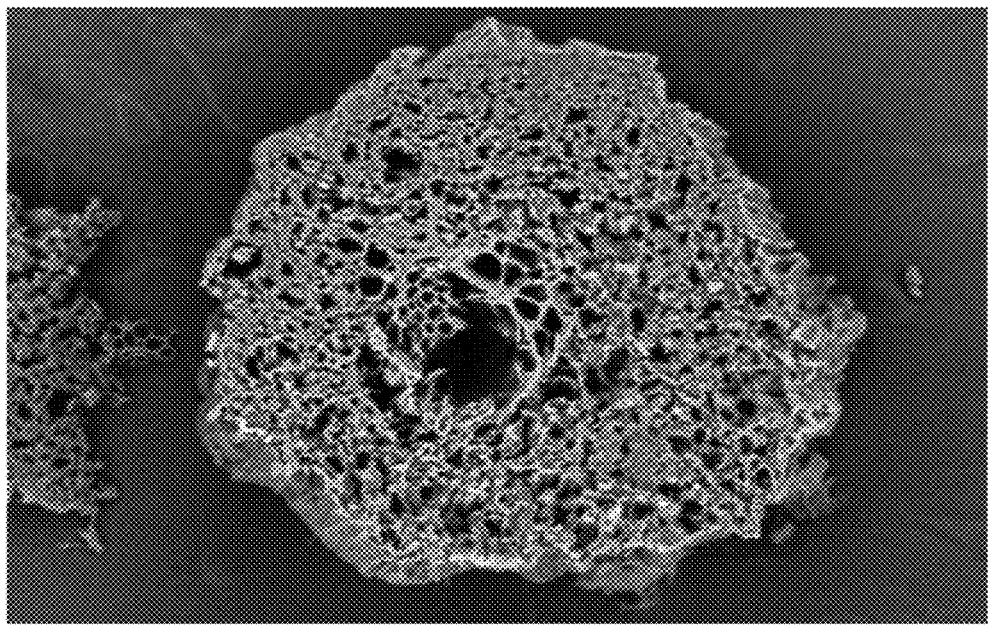
FIG. 5A is an electron image (300 µM resolution) of a cross section of a somatic embryo excised from a control, non-conditioned manufactured seed that was maintained at atmospheric pressure over a 48-hour time period, as described in Example 3.

Results:

FIG. 5A is a 300 μm resolution electron image of a cross section of a somatic embryo excised from a manufactured seed, after control treatment #2 (no pressure change).

Figure 5B:
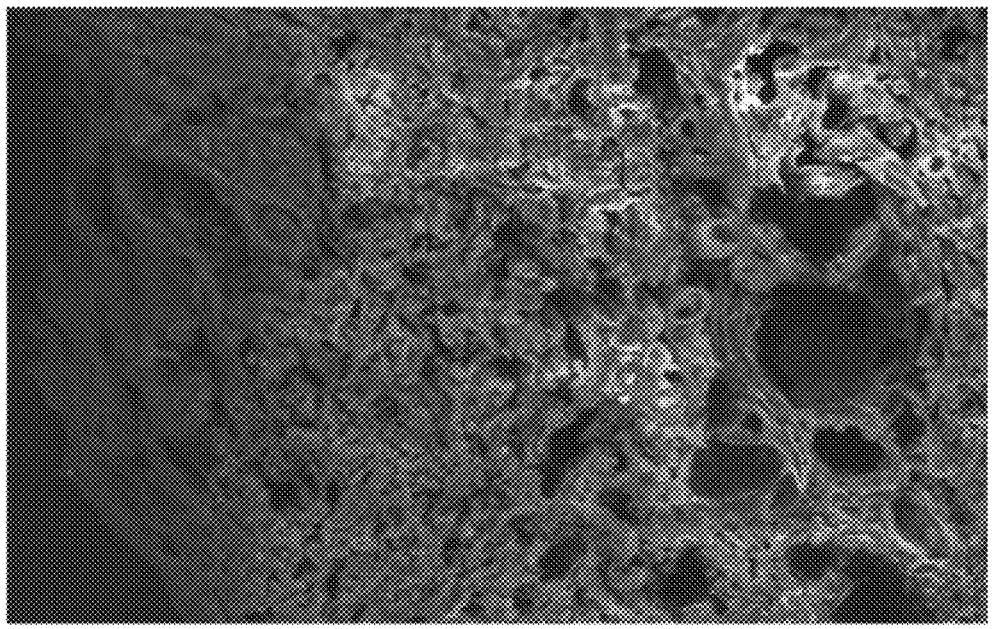
FIG. 5B is an electron image (100 µM resolution) of a cross section of an embryo excised from a conditioned manufactured seed after exposure to a cycle of positive and negative change in ambient pressure over a 48-hour time period, as described in Example 3.

FIG. 5B is a 100 μm resolution electron image of a cross section of a somatic embryo excised from a manufactured seed after pressure/vacuum treatment #1.

Figure 6A:
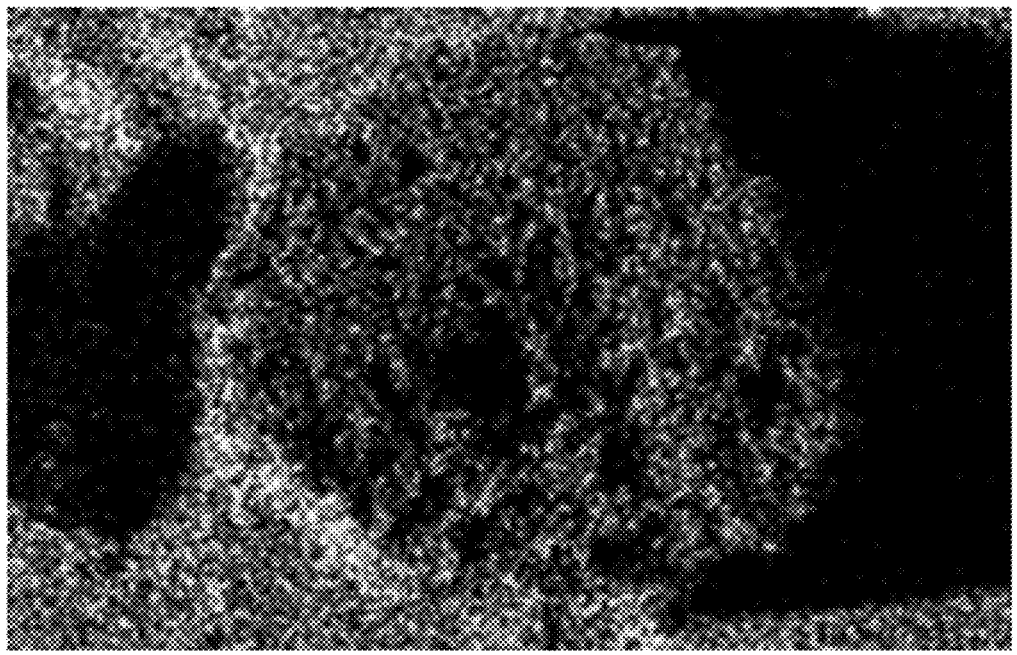
FIG. 6A is a carbon density map (300 µm resolution) of the image shown in FIG. 5A of the embryo from the control non-conditioned manufactured seed, showing a high level of carbon around the edges of the embryo, as described in Example 3.
Figure 6B:
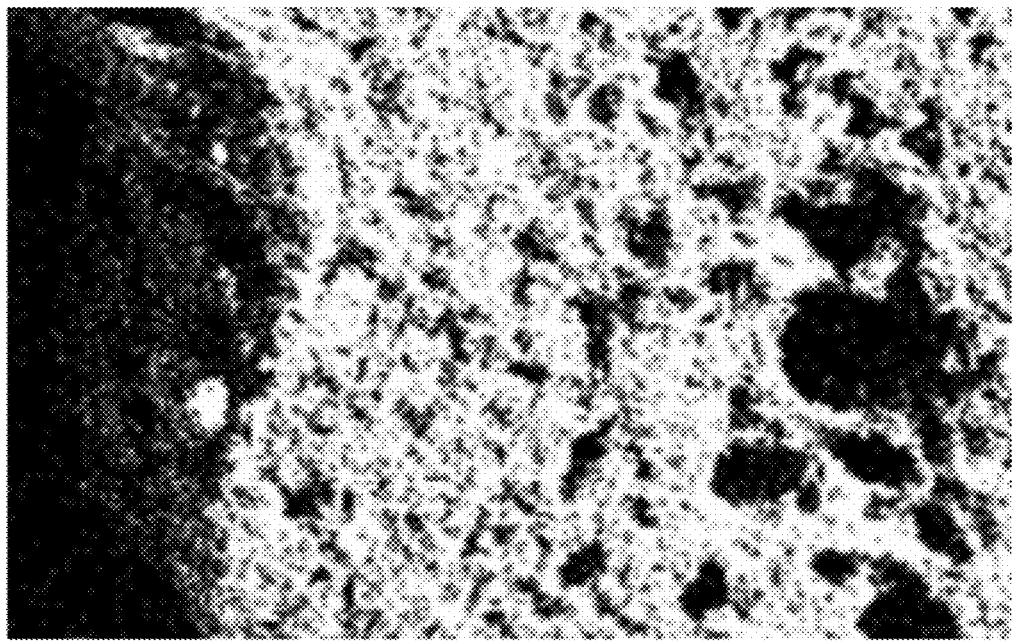
FIG. 6B is a carbon density map (100 µm resolution) of the image shown in FIG. 5B of the somatic embryo from a conditioned manufactured seed after exposure to a cycle of positive and negative change in ambient pressure over a 48-hour time period, showing a high level of carbon throughout the tissue, as described in Example 3.

FIG. 6A is a 300 μm resolution carbon density map of the image shown in FIG. 5A (somatic embryo excised from a manufactured seed, after control treatment #2 (no pressure change)). FIG. 6B is a 100 μm resolution carbon density map of the image shown in FIG. 5B (somatic embryo excised from a manufactured seed after pressure/vacuum treatment #1). The intensity of the white dots on the carbon density map indicate elemental presence. As shown in FIG. 6A, the embryo excised from the manufactured seed maintained at constant pressure (control treatment #2) has a high level of carbon, likely sugar, on the outside edges. In contrast, as shown in FIG. 6B, the embryo excised from the manufactured seed exposed to an increase and decrease in pressure (treatment #1) has carbon, likely sugar, perfused throughout the embryonic tissue.

Figure 7A:
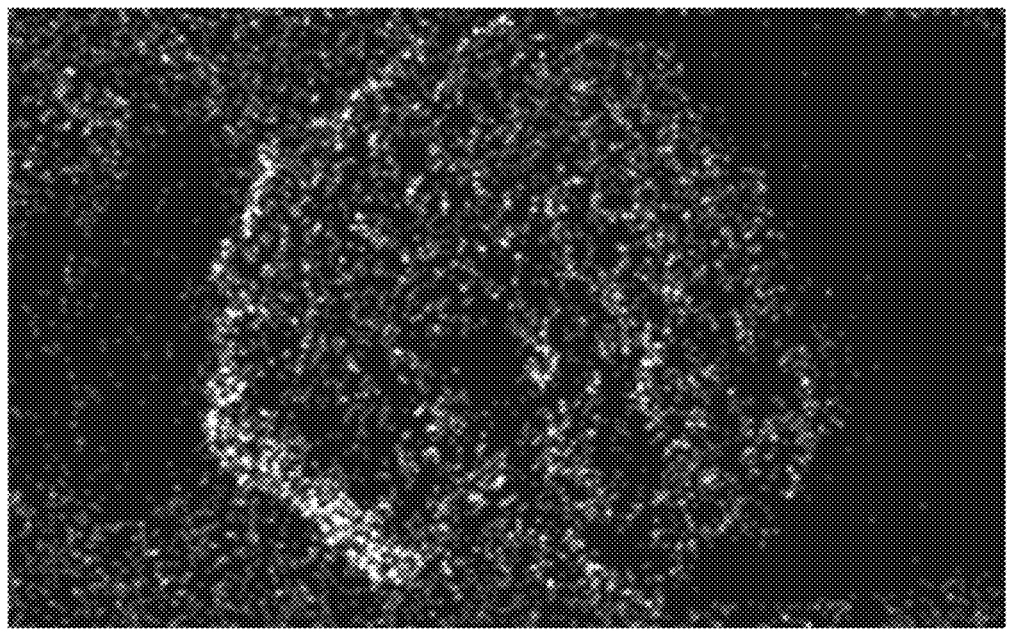
FIG. 7A is an oxygen density map (300 µm resolution) of the image shown in FIG. 5A of the somatic embryo from the control non-conditioned manufactured seed, showing a high level of oxygen around the edges of the embryo, as described in Example 3.
Figure 7B:
FIG. 7B is an oxygen density map (100 µm resolution) of the image shown in FIG. 5B of the somatic embryo from the conditioned manufactured seed after exposure to a cycle of positive and negative change in ambient pressure over a 48-hour time period, showing a high level of oxygen throughout the tissue, as described in Example 3.

FIG. 7A is 300 μm resolution oxygen density map of the image shown in FIG. 5A (somatic embryo excised from a manufactured seed, after control treatment #2 (no pressure change)). FIG. 7B is a 100 μm resolution oxygen density map of the image shown in FIG. 5B (somatic embryo excised from a manufactured seed after pressure/vacuum treatment #1). As shown in FIG. 7A, the embryo excised from the manufactured seed maintained at constant pressure (control treatment #2) has a high level of oxygen around the edges of the embryo. In contrast, as shown in FIG. 7B, the embryo excised from the manufactured seed exposed to an increase and decrease in pressure (treatment #1) has oxygen perfused throughout the embryonic tissue.

Figure 8A:
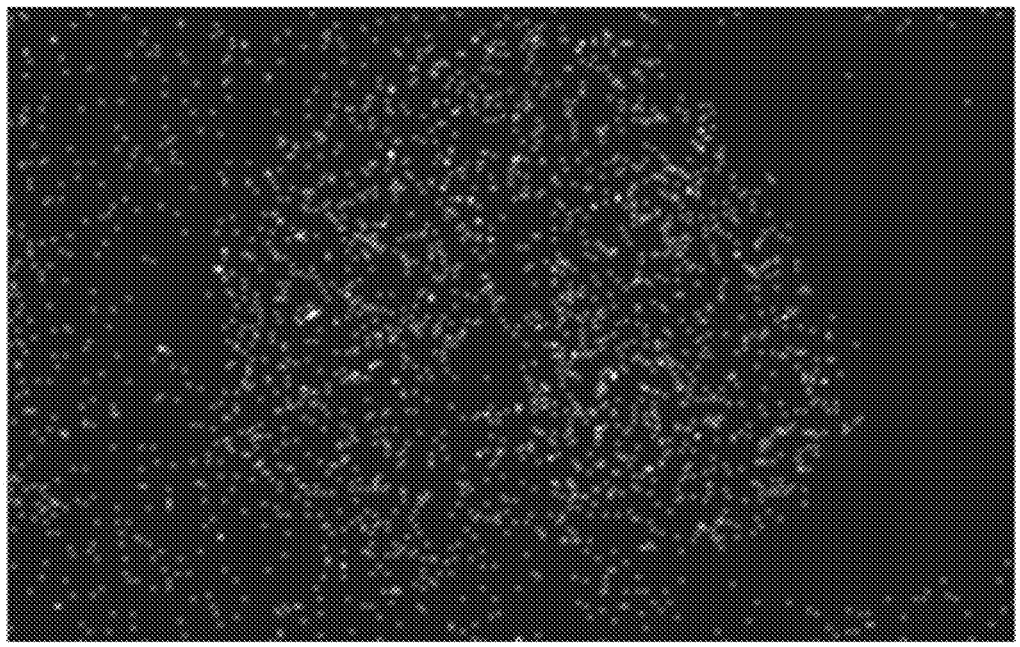
FIG. 8A is a phosphorus density map (300 µm resolution) of the image shown in FIG. 5A of the somatic embryo from the control non-conditioned manufactured seed, showing very little phosphorus in the embryo, as described in Example 3.
Figure 8B:
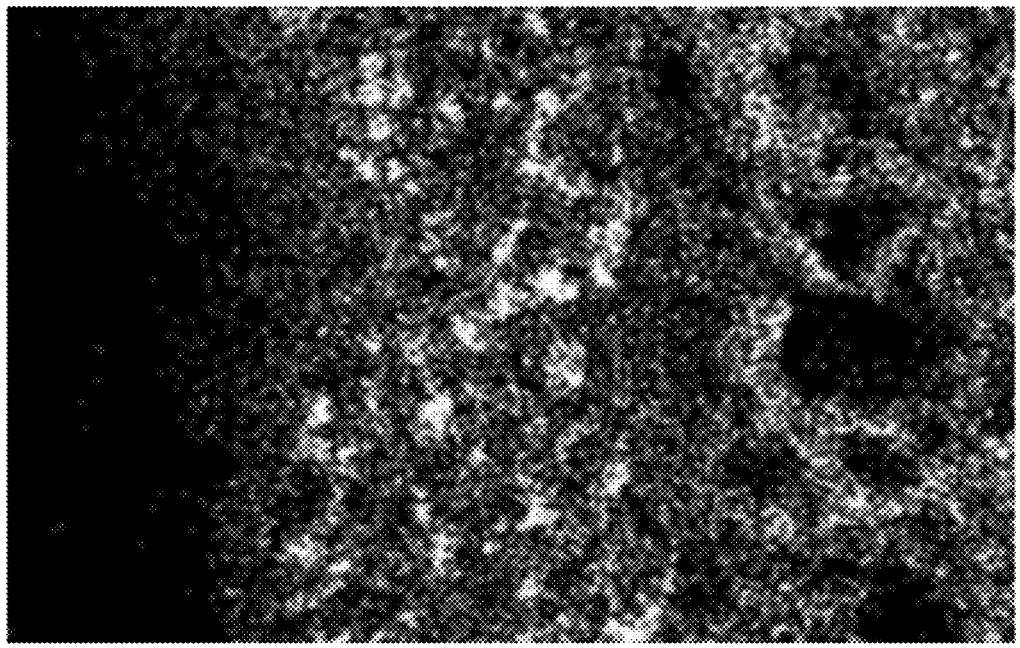
FIG. 8B is a phosphorus density map (100 µm resolution) of the image shown in FIG. 5B of the somatic embryo from the conditioned manufactured seed after exposure to a cycle of positive and negative change in ambient pressure over a 48-hour time period, showing a high level of phosphorus throughout the tissue, as described in Example 3.

FIG. 8A is a 300 μm resolution phosphorus density map of the image shown in FIG. 5A (somatic embryo excised from a manufactured seed, after control treatment #2 (no pressure change)). FIG. 8B is a 100 Tm resolution phosphorus density map of the image shown in FIG. 5B (somatic embryo excised from a manufactured seed after pressure/vacuum treatment #1). As shown in FIG. 8A, the embryo excised from the manufactured seed maintained at constant pressure (control treatment #2) has very little phosphorus in the embryo. In contrast, as shown in FIG. 8B, the embryo excised from the manufactured seed exposed to an increase and decrease in pressure (treatment #1) has a high density of phosphorus throughout the embryonic tissue. Similar patterns were observed for potassium density maps and for chlorine density maps in which the embryos excised from manufactured seeds exposed to pressure/vacuum (treatment #1) were observed to have substantially more density of the potassium or chlorine throughout the embryonic tissue as compared to the embryos excised from manufactured seeds treated with the control treatment #2 (data not shown).

Figure 9B:
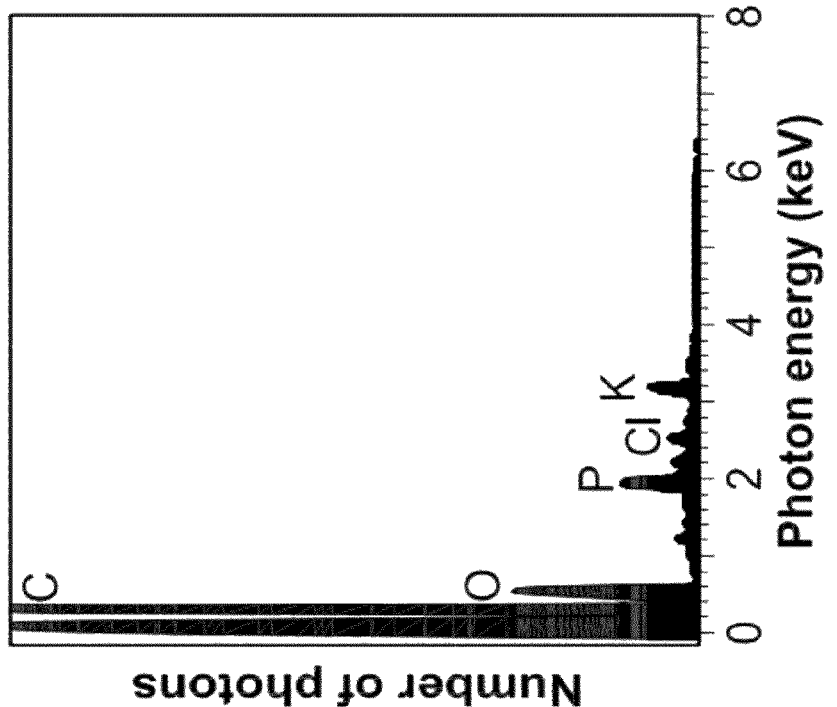
FIG. 9B graphically illustrates the sum of the signal spectra measured from the oxygen density map, phosphorus density map, chlorine density map, and the potassium density map for the somatic embryo excised from the conditioned manufactured seed after exposure to a cycle of positive and negative change in ambient pressure over a 48-hour time period, showing a higher level of oxygen, phosphorous, and potassium levels as compared to the control non-conditioned embryo shown in FIG. 9A, as described in Example 3.
Figure 9A:
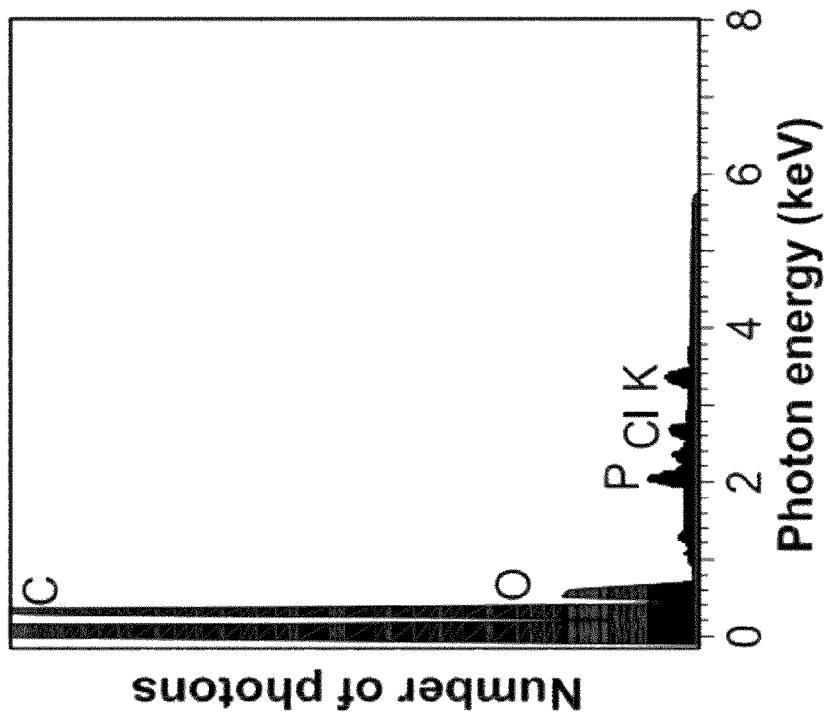
FIG. 9A graphically illustrates the sum of the signal spectra measured from the oxygen density map, phosphorus density map, chlorine density map, and the potassium density map for the embryo excised from the control non-conditioned manufactured seed, as described in Example 3.

FIG. 9A graphically illustrates the sum of the signal spectra measured from the oxygen density image, phosphorus density image, chlorine density image, and the potassium density image for the embryos excised from the manufactured seeds treated with the control treatment #2. The x-axis of FIG. 9A is photon energy, and the y-axis is the number of photons.

FIG. 9B graphically illustrates the sum of the signal spectra measured from the oxygen density image, phosphorus density image, chlorine density image, and the potassium density image for the embryos excised from the manufactured seeds exposed to an increase and decrease in pressure (treatment #1) demonstrating an increased amount of oxygen, phosphorous, and potassium levels as compared to the embryos excised from the manufactured seeds maintained at constant pressure shown in FIG. 9A. The x-axis of FIG. 9B is photon energy, and the y-axis is the number of photons.

The results shown in FIGS. 5A-9B are representative of the results observed for a total of three embryos tested.

In addition to the analysis of the embryonic tissue described above, sections of the embryo restraint ceramic material (FIG. 1 (32)) were taken from manufactured seeds before and after pressure/vacuum treatment, and it was observed that nutritive medium (26) was present in the restraint material (32) before and after pressure/vacuum treatment (data not shown).

In summary, the results in this example demonstrate that pressure and vacuum treatment of manufactured seeds resulted in an increased tissue concentration of nutrients in the embryos contained therein, including oxygen, phosphorus, chlorine, and potassium, in comparison to embryos excised from manufactured seeds that were maintained at constant pressure. While not wishing to be bound by any particular theory, these results are consistent with the theory that the pressure change increased nutrient perfusion into the embryo from the manufactured seed and increased movement from the gametophyte medium, thereby increasing the frequency of germination in comparison to manufactured seeds that were maintained at atmospheric pressure.

EXAMPLE 4

This example describes an experiment that was carried out to determine the effect of the length of time the manufactured seeds are exposed to a pressure change on the germination frequency.

Methods:

Manufactured seeds containing Loblolly Pine embryos of Genotype D were prepared as described in Example 1 and were subjected to the following treatment conditions:

1. A total of 13 manufactured seeds were exposed to the 48-hour pressure/vacuum cycling treatment #1, as described in Example 2 and shown in FIG. 3.

2. A total of 12 manufactured seeds were exposed to two quick cycles of pressure/vacuum treatment, each cycle lasting for one minute, wherein each cycle started from 0.00 PSI up to maximum pressure of +3.5 PSI and down to minimum pressure of −3.5 PSI.

3. A total of 12 manufactured seeds were exposed to one quick cycle, lasting for one minute, wherein the cycle started from 0.00 PSI up to a maximum of +3.5 PSI and down to a minimum of −3.5 PSI.

Germination

After the 48-hour treatments shown above, the manufactured seeds were placed in racks incubated in a mist box for a period of four days, and the percent germination, as measured by the presence of root emergence from the lid, was determined at day 4.

Figure 10:
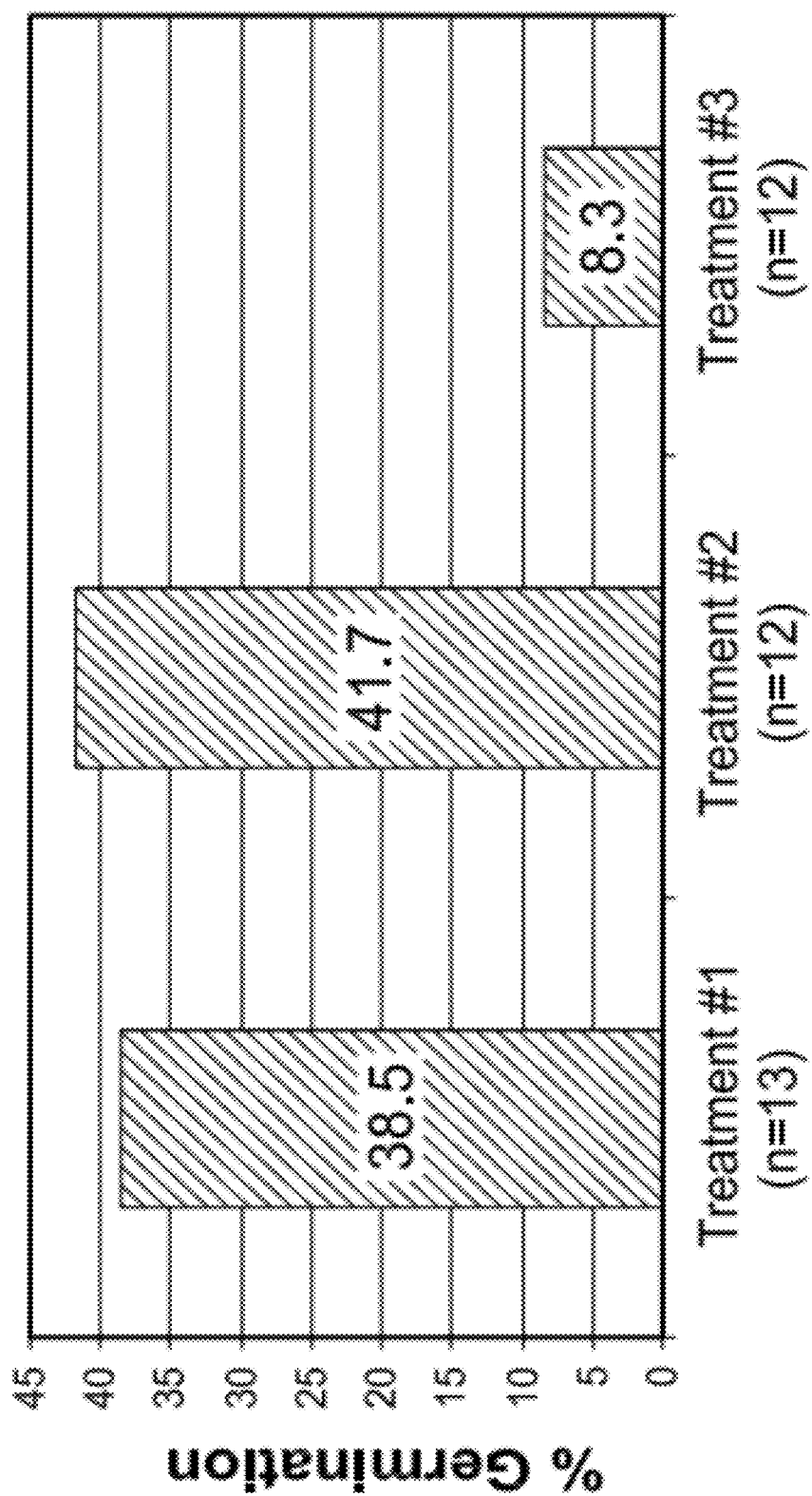
FIG. 10 graphically illustrates the percent root emergence (i.e., complete germination) of conditioned manufactured seeds subjected to alternating positive and negative changes in ambient pressure over a 48-hour time period in comparison to alternating positive and negative changes in ambient pressure over a two-minute time period, or a one-minute time period, respectively, as described in Example 4.

Results:

FIG. 10 graphically illustrates the percent germination (measured by root emergence) for manufactured seeds at four days after treatment #1, #2 and #3 described above. As shown in FIG. 10, exposure of the manufactured seeds to treatment #2 (two one-minute cycles of increased and decreased pressure), resulted in a germination frequency of 41.7%, which was at least as good as the germination frequency observed in manufactured seeds that were exposed to a 48-hour time period of increased and decreased pressure (38.5%). As further shown in FIG. 10, a single one-minute cycle (treatment #3) resulted in a germination frequency of 8.3%, and was therefore not as effective as treatment #1 or treatment #2. The results of this experiment demonstrates that multiple cycles of change in ambient pressure done rapidly (e.g., 60 to 120 seconds), are as effective as the very slow cycling treatment (48 hours) that was carried out in Example 2.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for conditioning a manufactured seed, the method comprising the steps of:
   (a) providing a plant somatic embryo having tissue, the plant somatic embryo being inserted into a manufactured seed, the manufactured seed comprising a manufactured seed coat comprising an orifice and nutritive media, such that the nutritive media is in functional contact with the plant somatic embryo; and
   (b) subjecting the manufactured seed to at least one change in ambient pressure for a period of time sufficient to generate a conditioned manufactured seed, conditioned manufactured seed having an increased germination frequency in comparison to a manufactured seed that was not subjected to at least one change in ambient pressure; wherein the at least one change in ambient pressure comprises a least one increase in ambient pressure relative to atmospheric pressure in the range of from about +0.05 PSI to about +4.0 PSI.

2. The method of claim 1, wherein the manufactured seed further comprises a lid covering the orifice of the seed coat thereby sealing the plant somatic embryo within the manufactured seed.

3. The method of claim 2, wherein at least one of the lid of the manufactured seed or the seed coat flexes when subjected to the change in ambient pressure.

4. The method of claim 1, wherein the at least one change in ambient pressure comprises at least one decrease in ambient pressure relative to atmospheric pressure in the range of from about −0.05 PSI to about −4.0 PSI.

5. The method of claim 1, wherein the at least one change in ambient pressure comprises at least one cycle comprising an increase in ambient pressure relative to atmospheric pressure for a first time period and a decrease in ambient pressure relative to atmospheric pressure for a second time period.

6. The method of claim 1, wherein the time period is at least one second.

7. The method of claim 1, wherein the time period is from about one second to about 96 hours.

8. The method of claim 1, wherein the manufactured seed further comprises a restraint and the embryo is disposed within the restraint.

9. The method of claim 8, wherein the restraint comprises packing material.

10. The method of claim 9, wherein the packing material comprises charcoal.

11. The method of claim 1, further comprising planting the conditioned manufactured seed into a growth medium.

12. The method of claim 1, wherein the nutritive media comprises at least one of a sugar, an amino acid, a phosphate ion, a chlorine ion, or a potassium ion.

13. The method of claim 12, further comprising the step of increasing within the plant somatic embryo's tissue at least one of sugar, amino acid, phosphate ion, chlorine ion, or potassium ion in comparison to an embryo from a manufactured seed that was not subjected to a change in ambient pressure.

14. The method of claim 1, wherein the plant somatic embryo is a conifer.

15. The method of claim 14, wherein the conifer is pine or Douglas-fir.

16. A method for producing seedlings or full grown plants from plant somatic embryos, comprising:
(a) inserting a plant somatic embryo into a manufactured seed comprising a manufactured seed coat comprising an orifice and nutritive media, such that the nutritive media is in functional contact with the plant somatic embryo;
(b) subjecting the manufactured seed comprising the embryo to at least one change in ambient pressure for a predetermined period of time to generate a conditioned manufactured seed; and
(c) planting the manufactured seed in a growth medium;
wherein the at least one change in ambient pressure comprises at least one cycle comprising an increase in ambient pressure relative to atmospheric pressure for a first time period and a decrease in ambient pressure relative to atmospheric pressure for a second time period.

17. The method of claim 16, further comprising sealing the embryo within the manufactured seed prior to step (b).

18. The method of claim 16, wherein the at least one change in ambient pressure comprises at least one increase in ambient pressure relative to atmospheric pressure in the range of from about +0.05 PSI to about +4.0 PSI.

19. The method of claim 16, wherein the at least one change in ambient pressure comprises at least one decrease in ambient pressure relative to atmospheric pressure in the range of from about −0.05 PSI to about −4.0 PSI.

20. The method of claim 16, wherein the time period is from about one second to about 96 hours.

* * * * *